(12) United States Patent
Haider et al.

(10) Patent No.: US 11,407,697 B2
(45) Date of Patent: *Aug. 9, 2022

(54) PROCESS FOR PRODUCING HIGH PURITY 1-BUTENE

(71) Applicant: SABIC Global Technologies B.V., Bergen op Zoom (NL)

(72) Inventors: Muhammad H. Haider, Riyadh (SA); Abdulaziz Al-Zahrani, Riyadh (SA); Te Chang, Sugar Land, TX (US)

(73) Assignee: SABIC GLOBAL TECHNOLOGIES B.V., Bergen op Zoom (NL)

(*) Notice: Subject to any disclaimer, the term of this patent is extended or adjusted under 35 U.S.C. 154(b) by 0 days.

This patent is subject to a terminal disclaimer.

(21) Appl. No.: 17/603,241

(22) PCT Filed: Apr. 28, 2020

(86) PCT No.: PCT/IB2020/054003
§ 371 (c)(1),
(2) Date: Oct. 12, 2021

(87) PCT Pub. No.: WO2020/240305
PCT Pub. Date: Dec. 3, 2020

(65) Prior Publication Data
US 2022/0144728 A1    May 12, 2022

Related U.S. Application Data

(60) Provisional application No. 62/855,719, filed on May 31, 2019.

(51) Int. Cl.
C07C 7/08      (2006.01)
C07C 5/333     (2006.01)
C07C 5/25      (2006.01)

(52) U.S. Cl.
CPC .............. C07C 7/08 (2013.01); C07C 5/2512 (2013.01); C07C 5/3337 (2013.01)

(58) Field of Classification Search
CPC . C07C 11/02; C07C 2/06; C07C 5/333; C10L 3/102; C10L 3/106; C10G 11/00;
(Continued)

(56) References Cited

U.S. PATENT DOCUMENTS 4,558,168 A * 12/1985 Gussow ................. C07C 11/08
585/314
11,168,041 B2 * 11/2021 Haider .................... C07C 5/333
2012/0010451 A1    1/2012 Di Girolamo et al.

FOREIGN PATENT DOCUMENTS

CN        102249837 A       11/2011
CN        104926587 A        9/2015
(Continued)

OTHER PUBLICATIONS

International Search Report and Written Opinion from PCT/IB2020/054003 dated Aug. 3, 2020, 8 pages.
(Continued)

*Primary Examiner* — Sharon Pregler
(74) *Attorney, Agent, or Firm* — Norton Rose Fulbright US LLP (57) ABSTRACT

Methods of and systems for producing an olefin are disclosed. A paraffin is dehydrogenated to produce a mixture comprising the olefin and unreacted paraffin. The mixture is then fed to an extractive distillation unit that uses soybean oil as a solvent to extract at least some n-butane from the mixture.

16 Claims, 3 Drawing Sheets

(58) Field of Classification Search
CPC .. C10G 2300/1025; C10G 50/00; C10G 5/00; F25J 1/0022; F25J 2200/78; F25J 2205/02; F25J 2205/50; F25J 2210/62; F25J 2215/04; F25J 2215/60
See application file for complete search history.

(56) References Cited

FOREIGN PATENT DOCUMENTS

| | | |
|---|---|---|
| FR | 2493306 A1 | 5/1982 |
| GB | 881597 A | 11/1961 |
| WO | WO2005042449 A1 | 5/2005 |
| WO | WO2020030995 A1 | 2/2020 |
| WO | WO2020240357 A1 | 12/2020 |

OTHER PUBLICATIONS

Tres et al. "Low-pressure solubility of propane and n-butane in refined soybean oil." J. Chem. Thermodynamics 41 (2009) 1378-1381.

* cited by examiner

PROCESS FOR PRODUCING HIGH PURITY 1-BUTENE

CROSS REFERENCE TO RELATED APPLICATIONS

This application is a national phase application under 35 U.S.C. § 371 of International Application No. PCT/IB2020/054003 filed Apr. 28, 2020, which claims priority to U.S. Provisional Patent Application No. 62/855,719 filed May 31, 2019. The entire contents of each of the above-referenced disclosures is specifically incorporated by reference herein without disclaimer.

FIELD OF INVENTION

The present invention generally relates to systems and methods for producing an olefin. More specifically, the present invention relates to systems and methods that use soybean oil as a solvent to separate a paraffin from one or more olefins in an extractive distillation unit.

BACKGROUND OF THE INVENTION $C_4$ olefins, such as isobutene, 1-butene, trans-2-butene, and cis-2-butene, are a group of $C_4$ hydrocarbons that can be used in various chemical production processes. For instance, isobutene is used for MTBE synthesis by etherification with methanol in the presence of an acidic catalyst. 1-butene can be readily used for producing polybutene via polymerization. Furthermore, 1-butene can be used as a co-monomer in the production of polyethylene. 2-butenes (including trans-2-butene and cis-2-butene) can be used for producing propylene via metathesis and for producing gasoline, butadiene, and/or butanone.

Conventionally, $C_4$ olefins are produced by separating crude $C_4$ refinery streams. However, these crude $C_4$ streams generally contain a large amount of $C_4$ paraffins, resulting in high energy consumption in processing these $C_4$ streams and low production efficiency for the $C_4$ olefins. Additionally, purifying the 1-butene and 2-butenes obtained from these crude $C_4$ refinery streams consumes a large amount of energy and requires large distillation columns due to close boiling points of these $C_4$ olefins. In sum, the overall production cost for producing high purity $C_4$ olefins by separating $C_4$ refinery streams is high. Another method of producing 1-butene includes dimerization of ethylene. However, the feedstock of this method is ethylene, which is in high demand as a feedstock in the processes of producing various high-value polymeric products. Therefore, using high-valued ethylene for the production of 1-butene can be cost prohibitive.

Overall, while the methods of producing purified $C_4$ olefins exist, the need for improvements in this field persists in light of at least the aforementioned drawbacks for the conventional methods.

BRIEF SUMMARY OF THE INVENTION

A solution to at least some of the above mentioned problems associated with systems and methods for producing $C_4$ olefins has been discovered. The solution resides in a method of producing $C_4$ olefins by dehydrogenating n-butane and further separating the resulting $C_4$ hydrocarbons. Notably, the use of n-butane as the feedstock in this method is more economically suitable than the conventional methods that utilize ethylene dimerization to produce $C_4$ olefins. Furthermore, the method includes using soybean oil as a solvent to extract unreacted n-butane from the $C_4$ hydrocarbons in an extractive distillation unit, which is more environmentally friendly than the conventional methods that use toxic organic solvents. Moreover, the method can include isomerizing 2-butene produced by dehydrogenation of n-butane to form 1-butene, thereby substantially eliminating the need for separating 1-butene from 2-butene in the downstream separation process, resulting in significant reduction in energy consumption for separating $C_4$ olefins compared to conventional methods. Therefore, the method of the present invention provides a technical solution to at least some of the problems associated with the conventional methods for producing $C_4$ olefins.

Embodiments of the invention include a method of producing an olefin. The method comprises dehydrogenating a paraffin to produce a mixture comprising the olefin and unreacted paraffin. The method comprises contacting the mixture with soybean oil under conditions such that the unreacted paraffin dissolves in the soybean oil at a higher rate than the olefin to form (1) a first stream comprising the soybean oil and at least some of the unreacted paraffin of the mixture and (2) a second stream comprising primarily the olefin.

Embodiments of the invention include a method of producing an olefin. The method comprises dehydrogenating a paraffin to produce a mixture comprising the olefin and unreacted paraffin. The method comprises contacting the mixture with soybean oil in an extractive distillation column under conditions such that the unreacted paraffin dissolves in the soybean oil at a higher rate than the olefin to form (1) a first stream comprising the soybean oil and at least 50 wt. % of the unreacted paraffin of the mixture and (2) a second stream comprising primarily the olefin. The conditions in the contacting step comprise a temperature of 10 to 50° C. The method comprises separating the olefin from the second stream.

Embodiments of the invention include a method of producing 1-butene. The method comprises dehydrogenating, in a dehydrogenation zone, n-butane to produce a first mixture comprising 1-butene, 2-butene, isobutene, and unreacted n-butane. The method comprises processing, in an isomerization zone, the first mixture under isomerization conditions sufficient to isomerize 2-butene to form 1-butene. The method further comprises contacting an effluent of the isomerization zone with soybean oil in an extractive distillation unit under extractive distillation conditions such that the unreacted n-butane dissolves in the soybean oil at a higher rate than the 1-butene and the isobutene to form (1) a first stream comprising the soybean oil and at least some of the unreacted n-butane of the first mixture and (2) a second stream comprising primarily 1-butene and isobutene. The method further still comprises separating the second stream to produce a third stream comprising primarily 1-butene.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

Currently, $C_4$ olefins are produced by separating $C_4$ refinery streams that contain $C_4$ olefins and a large amount of $C_4$ paraffins. The energy consumption for separating these streams and producing high purity $C_4$ olefins is generally high due to close boiling points of the components in the $C_4$ refinery stream, such as 1-butene and 2-butene. Furthermore, toxic organic solvents are generally used for extracting $C_4$ olefins from $C_4$ refinery streams, resulting in high pollution risk to the environment. Another conventional method of producing $C_4$ olefins includes dimerization of ethylene. However, the feedstock ethylene in the dimerization process is in high demand for producing various high-value chemicals. Thus, using ethylene to produce $C_4$ olefins can be cost prohibitive. N-butane dehydrogenation can be used for producing $C_4$ olefins, but the product stream of this process includes various $C_4$ hydrocarbons of similar boiling points, which are difficult to separate from each other, resulting in high production cost for $C_4$ olefins. The present invention provides a solution to at least some of these problems. The solution is premised on a method that includes dehydrogenating n-butane to produce a $C_4$ mixture and extractive-distilling of unreacted n-butane from the $C_4$ mixture. This can be beneficial for at least reducing the cost for feedstocks compared to conventional methods that produce $C_4$ olefins via ethylene dimerization. Furthermore, the use of soybean oil as a solvent in extractive distillation process can mitigate the negative impact to the environment compared to conventional methods that use toxic organic solvents. Furthermore, the disclosed method can include isomerizing 2-butene in the $C_4$ mixture to produce 1-butene, thereby eliminating the need for separating 1-butene from 2-butene, resulting in reduced energy consumption for producing $C_4$ olefins. These and other non-limiting aspects of the present invention are discussed in further detail in the following sections.

A. System of Producing Olefin

Figure 1:
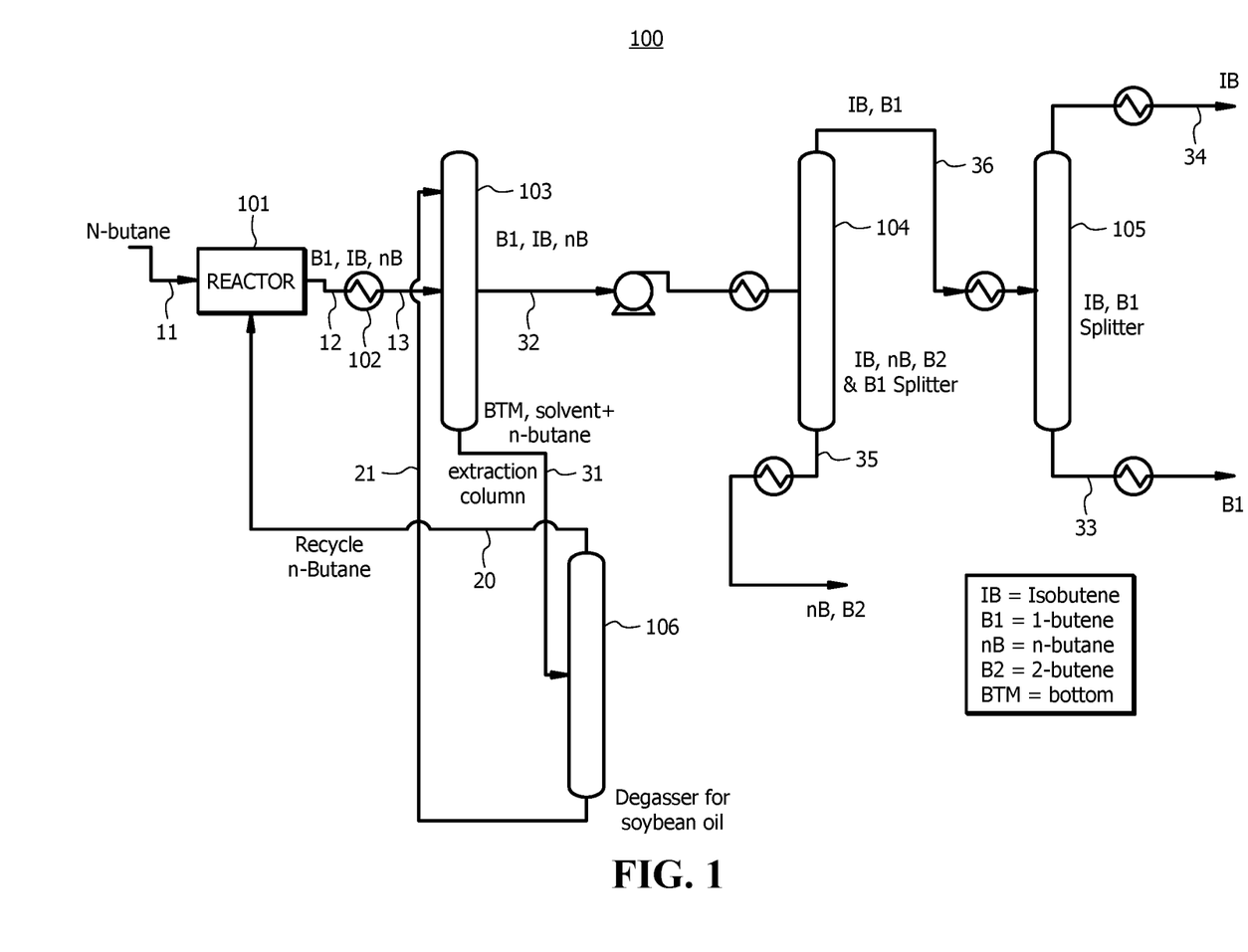
FIG. 1 shows a schematic diagram of a system for producing an olefin, according to embodiments of the invention.

In embodiments of the invention, the system for producing olefin can include a reaction unit, an extractive-distillation unit, and two distillation columns. With reference to FIG. 1, a schematic diagram is shown of system 100 that is configured to produce an olefin with reduced energy consumption and reduced negative environmental impact compared to conventional methods. According to embodiments of the invention, system 100 includes reaction unit 101.

According to embodiments of the invention, reaction unit 101 is configured to receive feed stream 11 comprising a paraffin and react the paraffin to produce one or more olefins, as isomers. In embodiments of the invention, reaction unit 101 may include a dehydrogenation zone adapted to dehydrogenate the paraffin to produce one or more olefins as isomers. Reaction unit 101 may further include an isomerization zone adapted to isomerize one or more of the olefins to produce one or more corresponding isomers. According to embodiments of the invention, the dehydrogenation zone and the isomerization zone may be included in a single reactor. In embodiments of the invention, the dehydrogenation zone and the isomerization zone may be included in separate reactors in series. In embodiments of the invention, the dehydrogenation zone may include a dehydrogenation catalyst comprising platinum/tin, palladium, gallium, or combinations thereof. The isomerization zone may include an isomerization catalyst comprising alumina, alpha ($\alpha$)-alumina, ($\beta$)-alumina theta ($\theta$)-alumina, gamma ($\gamma$)-alumina, eta (η)-alumina, or combinations thereof. Effluent stream 12 of reaction unit 101 may include unreacted paraffin, and the one or more olefins.

In embodiments of the invention, an outlet of reaction unit 101 may be in fluid communication with an inlet of cooler 102 such that effluent stream 12 flows from reaction unit 101 to cooler 102. Cooler 102 is configured to cool effluent stream 12 to form cooled effluent stream 13. According to embodiments of the invention, cooled effluent stream 13 may be at a temperature of 20 to 30° C. and all ranges and values there between including ranges of 20 to 21° C., 21 to 22° C., 22 to 23° C., 23 to 24° C., 24 to 25° C., 25 to 26° C., 26 to 27° C., 27 to 28° C., 28 to 29° C., and 29 to 30° C. In embodiments of the invention, cooler 102 comprises one or more heat exchangers.

In embodiments of the invention, an outlet of cooler 102 is in fluid communication with an inlet of extractive distillation unit 103 such that cooled effluent stream 13 flows from cooler 102 to extractive distillation unit 103. In embodiments of the invention, extractive distillation unit 103 includes one or more extractive distillation columns. Extractive distillation unit 103 is configured to separate cooled effluent stream 13, via extractive distillation, to produce (1) first stream 31 comprising at least some of the unreacted paraffin and (2) second stream 32 comprising one or more of the olefins. In embodiments of the invention, extractive distillation unit 103 uses soybean oil as a solvent for extractive distillation. First stream 31, in embodiments of the invention, further comprises the solvent. Second stream 32 may further comprise the paraffin.

In embodiments of the invention, an outlet of extractive distillation unit 103 is in fluid communication with first distillation unit 104 such that second stream 32 flows from extractive distillation unit 103 to first distillation unit 104. According to embodiments of the invention, when second stream 32 comprises two or more olefins and first distillation unit 104 is configured to separate second stream 32 to produce fifth stream 35 comprising the paraffin and sixth stream 36 comprising the two or more olefins. First distillation unit 104 may include one or more distillation columns. According to embodiments of the invention, an outlet of first distillation unit 104 is in fluid communication with second distillation unit 105 such that sixth stream 36 flows from first distillation unit 104 to second distillation unit 105.

According to embodiments of the invention, second distillation unit 105 is configured to separate sixth stream 36 to produce third stream 33 and fourth stream 34. In embodiments of invention, second distillation unit 105 may comprise one or more distillation columns. Third stream 33 may be a bottom stream from second distillation unit 105. Fourth stream 34 may be a top stream of second distillation unit 105. In embodiments of the invention, third stream 33 includes the olefin. Fourth stream 34 may include one or more olefins as the isomer(s) of the olefin of third stream 33. In embodiments of the invention, each of first distillation unit 104 and second distillation unit 105 comprises one or more distillation columns that have a theoretical plate number in a range of 150 to 200 and all ranges and values there between including ranges of 150 to 155, 155 to 160, 160 to 165, 165 to 170, 170 to 175, 175 to 180, 180 to 185, 185 to 190, 190 to 195, and 195 to 200.

In embodiments of the invention, an outlet of extractive distillation unit 103 is in fluid communication with an inlet of degasser 106 such that first stream 31 flows from extractive distillation unit 103 to degasser 106. In embodiments of the invention, degasser 106 is configured to separate first stream 31 to produce gaseous stream 20 and liquid stream 21. Gaseous stream 20 may comprise primarily the paraffin. Liquid stream 21 may comprise primarily the solvent. Degasser 106 may comprise an extractive distillation column operating at 0.5 to 2 bar and at 65 to 90° C. According to embodiments of the invention, an outlet of degasser 106 is in fluid communication with an inlet of extractive distillation unit 103 such that liquid stream 21 comprising primarily the solvent is recycled to extractive distillation unit 103. According to embodiments of the invention, an outlet of degasser 106 is in fluid communication with an inlet of reaction unit 101 such that gaseous stream 20 comprising primarily the paraffin is recycled to reaction unit 101.

In embodiments of the invention, non-limiting examples of the paraffin include n-butane, propane, ethane. Non-limiting examples for the one or more olefins may include 1-butene, 2-butene, isobutene, and combinations thereof. According to embodiments of the invention, the dehydrogenation zone of reaction unit 101 is configured to dehydrogenate n-butane to produce 1-butene, 2-butene, isobutene, or combinations thereof. The isomerization zone of reaction unit 101 may be configured to isomerize 2-butene to produce 1-butene. According to embodiments of the invention, effluent stream 12 from reaction unit 101 may comprise unreacted n-butane, 1-butene, isobutene, or combinations thereof. Effluent stream 12 from reaction unit 101 may further include less than 0.1 wt. % (trace amount) of 2-butene. In embodiments of the invention, sixth stream 36 from first distillation unit 104 comprises primarily 1-butene and isobutene, collectively. Fifth stream 35 from first distillation unit 104 may comprise primarily n-butane. Fifth stream 35 may further comprise less than 40 to 50 wt. % 2-butene. According to embodiments of the invention, third stream 33 from second distillation unit 105 comprises primarily 1-butene. Fourth stream 34 from second distillation unit 105 may comprise primarily isobutene.

B. Method of Producing Olefin

Figure 2:
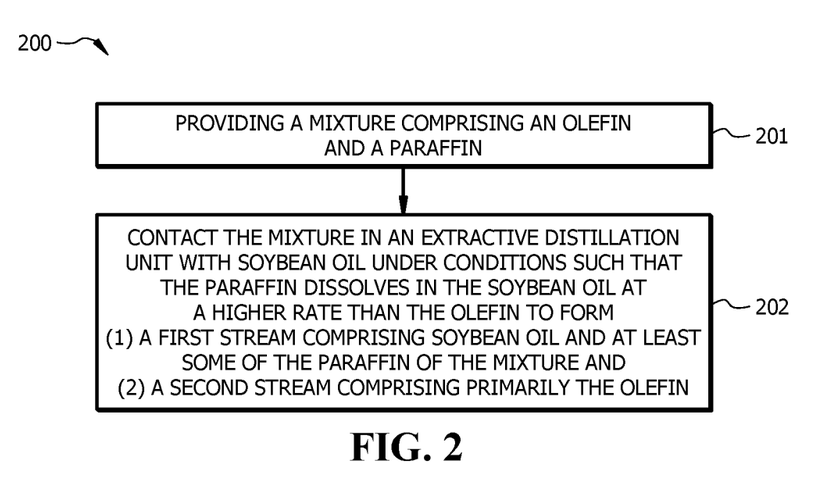
FIG. 2 shows a schematic flowchart for a method of producing an olefin, according to embodiments of the invention.

Methods of producing an olefin that includes using soybean oil as a solvent in an extractive distillation column have been discovered. Embodiments of the methods are capable of reducing the use of toxic solvents for extractive distillation and reducing the overall energy consumption for producing an olefin compared to conventional methods. As shown in FIG. 2, embodiments of the invention include method 200 for producing a first olefin. Method 200 may be implemented by system 100, as shown in FIG. 1.

According to embodiments of the invention, as shown in block 201, method 200 includes providing a mixture comprising the first olefin and a paraffin. In embodiments of the invention, providing at block 201 includes dehydrogenating, in the dehydrogenation zone of reaction unit 101, the paraffin to produce a first olefin. In embodiments of the invention, exemplary paraffins include n-butane, propane, ethane, and combinations thereof. In embodiments of the invention, the dehydrogenating is performed at a dehydrogenation temperature of 400 to 550° C. and all ranges and values there between including ranges of 400 to 410° C., 410 to 420° C., 420 to 430° C., 430 to 440° C., 440 to 450° C., 450 to 460° C., 460 to 470° C., 470 to 480° C., 480 to 490° C., 490 to 500° C., 500 to 510° C., 510 to 520° C., 520 to 530° C., 530 to 540° C., and 540 to 550° C. Dehydrogenating may be performed at a dehydrogenation pressure of 0 to 15 bar and all ranges and values there between including ranges of 0 to 1 bar, 1 to 2 bar, 2 to 3 bar, 3 to 4 bar, 4 to 5 bar, 5 to 6 bar, 6 to 7 bar, 7 to 8 bar, 8 to 9 bar, 9 to 10 bar, 10 to 11 bar, 11 to 12 bar, 12 to 13 bar, 13 to 14 bar, and 14 to 15 bar. In embodiments of the invention, dehydrogenating is performed at a weight hourly space velocity of 1000 to 4000 hr$^{-1}$ and all ranges and values there between including ranges of 1000 to 1200 hr$^{-1}$, 1200 to 1400 hr$^{-1}$, 1400 to 1600 hr$^{-1}$, 1600 to 1800 hr$^{-1}$, 1800 to 2000 hr$^{-1}$, 2000 to 2200 hr$^{-1}$, 2200 to 2400 hr$^{-1}$, 2400 to 2600 hr$^{-1}$, 2600 to 2800 hr$^{-1}$, 2800 to 3000 hr$^{-1}$, 3000 to 3200 hr$^{-1}$, 3200 to 3400 hr$^{-1}$, 3400 to 3600 hr$^{-1}$, 3600 to 3800 hr$^{-1}$, and 3800 to 4000 hr$^{-1}$.

According to embodiments of the invention, the dehydrogenating step produces the first olefin and a second olefin as isomers, the providing at block 201 further comprises isomerizing the second olefin, in the isomerization zone of reaction unit 101, to produce an additional amount of the first olefin. In embodiments of the invention, the isomerizing step is performed at a isomerization temperature of 400 to 550° C. and all ranges and values there between including ranges of 400 to 410° C., 410 to 420° C., 420 to 430° C., 430 to 440° C., 440 to 450° C., 450 to 460° C., 460 to 470° C., 470 to 480° C., 480 to 490° C., 490 to 500° C., 500 to 510° C., 510 to 520° C., 520 to 530° C., 530 to 540° C., and 540 to 550° C. The isomerizing step may be performed at a dehydrogenation pressure of 0 to 15 bar and all ranges and values there between including ranges of 0 to 1 bar, 1 to 2 bar, 2 to 3 bar, 3 to 4 bar, 4 to 5 bar, 5 to 6 bar, 6 to 7 bar, 7 to 8 bar, 8 to 9 bar, 9 to 10 bar, 10 to 11 bar, 11 to 12 bar, 12 to 13 bar, 13 to 14 bar, and 14 to 15 bar. In embodiments of the invention, the isomerizing step is performed at a weight hourly space velocity of 1000 to 4000 hr$^{-1}$ and all ranges and values there between including ranges of 1000 to 1200 hr$^{-1}$, 1200 to 1400 hr$^{-1}$, 1400 to 1600 hr$^{-1}$, 1600 to 1800 hr$^{-1}$, 1800 to 2000 hr$^{-1}$, 2000 to 2200 hr$^{-1}$, 2200 to 2400 hr$^{-1}$, 2400 to 2600 hr$^{-1}$, 2600 to 2800 hr$^{-1}$, 2800 to 3000 hr$^{-1}$, 3000 to 3200 hr$^{-1}$, 3200 to 3400 hr$^{-1}$, 3400 to 3600 hr$^{-1}$, 3600 to 3800 hr$^{-1}$, and 3800 to 4000 hr$^{-1}$.

According to embodiments of the invention, as shown in block 202, method 200 comprises contacting the mixture, in extractive distillation unit 103, with soybean oil under conditions such that the paraffin dissolves in the soybean oil at a higher rate than the first olefin to form (1) first stream 31 comprising soybean oil and at least some of the paraffin of the mixture and (2) second stream 32 comprising primarily the first olefin. In embodiments of the invention, conditions at block 202 comprise a temperature of 10 to 50° C. and all ranges and values there between including ranges of 10 to 12° C., 12 to 14° C., 14 to 16° C., 16 to 18° C., 18 to 20° C., 20 to 22° C., 22 to 24° C., 24 to 26° C., 26 to 28° C., 28 to 30° C., 30 to 32° C., 32 to 34° C., 34 to 36° C., 36 to 38° C., 38 to 40° C., 40 to 42° C., 42 to 44° C., 44 to 46° C., 46 to 48° C., and 48 to 50° C. In embodiments of the invention, the conditions at block 202 include an operating pressure of extractive distillation unit 103 in a range of 3 to 5 bar and all ranges and values there between including ranges of 3 to 3.2 bar, 3.2 to 3.4 bar, 3.4 to 3.6 bar, 3.6 to 3.8 bar, 3.8 to 4.0 bar, 4.0 to 4.2 bar, 4.2 to 4.4 bar, 4.4 to 4.6 bar, 4.6 to 4.8 bar, and 4.8 to 5.0 bar. The conditions, in embodiments of the invention, at block 202 may include a flow rate ratio of the mixture to the soybean oil being fed into extractive distillation unit 103 in a range of 5 to 15 and all ranges and values there between including ranges of 5 to 6, 6 to 7, 7 to 8, 8 to 9, 9 to 10, 10 to 11, 11 to 12, 12 to 13, 13 to 14, and 14 to 15.

Figure 3:
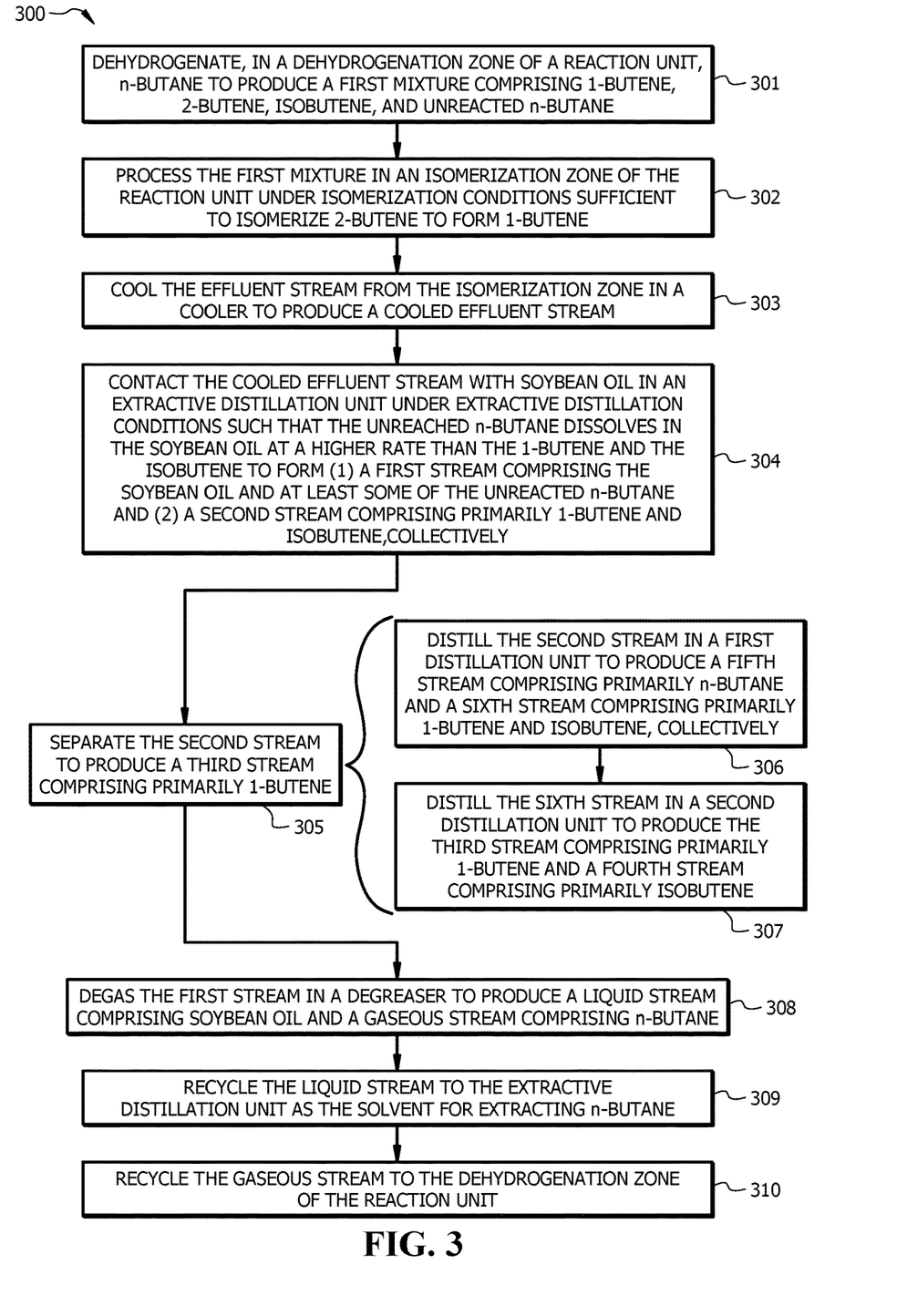
FIG. 3 shows a schematic flowchart for a method of producing 1-butene from n-butane, according to embodiments of the invention.

According to embodiments of the invention, the paraffin is n-butane and the method for producing a first olefin includes method 300 for producing 1-butene. Method 300 may be implemented by system 100 as shown in FIG. 1. According to embodiments of the invention, as shown in block 301, method 300 includes dehydrogenating, in the dehydrogenation zone of reaction unit 101, n-butane to produce a first mixture comprising 1-butene, 2-butene, isobutene, and unreacted n-butene. In embodiments of the invention, the dehydrogenating at block 301 is performed at a dehydrogenation temperature in a range of 400 to 550° C. and all ranges and value there between including ranges of 400 to 410° C., 410 to 420° C., 420 to 430° C., 430 to 440° C., 440 to 450° C., 450 to 460° C., 460 to 470° C., 470 to 480° C., 480 to 490° C., 490 to 500° C., 500 to 510° C., 510 to 520° C., 520 to 530° C., 530 to 540° C., and 540 to 550° C. Dehydrogenating at block 301 may be performed at a dehydrogenation pressure of 0 to 15 bar and all ranges and values there between including ranges of 0 to 1 bar, 1 to 2 bar, 2 to 3 bar, 3 to 4 bar, 4 to 5 bar, 5 to 6 bar, 6 to 7 bar, 7 to 8 bar, 8 to 9 bar, 9 to 10 bar, 10 to 11 bar, 11 to 12 bar, 12 to 13 bar, 13 to 14 bar, and 14 to 15 bar. In embodiments of the invention, dehydrogenating at block 301 is performed at a weight hourly space velocity of 1000 to 4000 hr$^{-1}$ and all ranges and values there between including ranges of 1000 to 1200 hr$^{-1}$, 1200 to 1400 hr$^{-1}$, 1400 to 1600 hr$^{-1}$, 1600 to 1800 hr$^{-1}$, 1800 to 2000 hr$^{-1}$, 2000 to 2200 hr$^{-1}$, 2200 to 2400 hr$^{-1}$, 2400 to 2600 hr$^{-1}$, 2600 to 2800 hr$^{-1}$, 2800 to 3000 hr$^{-1}$, 3000 to 3200 hr$^{-1}$, 3200 to 3400 hr$^{-1}$, 3400 to 3600 hr$^{-1}$, 3600 to 3800 hr$^{-1}$, and 3800 to 4000 hr$^{-1}$.

According to embodiments of the invention, method 300 includes processing, in the isomerization zone of reaction unit 101, the first mixture under isomerization conditions sufficient to isomerize 2-butene to form 1-butene, as shown in block 302. In embodiments of the invention, about 30 to 50 wt. % 2-butene of the first mixture is isomerized to produce 1-butene. The isomerizing at block 302 may be performed at an isomerization temperature in a range of 400 to 550° C. and all ranges and values there between. The isomerizing at block 302 may be performed at an isomerization pressure in a range of 10 to 15 bar and all ranges and values there between. In embodiments of the invention, the isomerizing at block 302 is performed at a weight hourly space velocity in a range of 1000 to 4000 hr$^{-1}$ and all ranges and values there between.

According to embodiments of the invention, as shown in block 303, method 300 includes cooling effluent stream 12 from the isomerization zone in cooler 102 to produce cooled effluent stream 13. In embodiments of the invention, effluent stream 12 from the isomerization zone includes 50 to 60 wt. % 1-butene, 40 to 50 wt. % unreacted n-butane, and 0.1 to 0.5 wt. % isobutene. Effluent stream 12 may further comprise less than 0.1 wt. % 2-butene. In embodiments of the invention, cooled effluent stream 13 is at a temperature of 23 to 30° C. and all ranges and values there between including ranges of 23 to 24° C., 24 to 25° C., 25 to 26° C., 26 to 27° C., 27 to 28° C., 28 to 29° C., and 29 to 30° C.

In embodiments of the invention, as shown in block 304, method 300 includes contacting cooled effluent stream 13 with soybean oil in extractive distillation unit 103 under extractive distillation conditions such that the unreacted n-butane dissolves in the soybean oil at a higher rate than the 1-butene and the isobutene to form (1) first stream 31 comprising the soybean oil and at least some of the unreacted n-butane and (2) second stream 32 comprising primarily 1-butene and isobutene, collectively. In embodiments of the invention, first stream 31 comprises at least 50 wt. % of the unreacted n-butane from the first mixture. First stream 31 may comprise at least 70 wt. % of the unreacted n-butane from the first mixture.

In embodiments of the invention, at block 304, extractive distillation conditions includes an overhead boiling range of 20 to 30° C. and all ranges and values there between including 20 to 21° C., 21 to 22° C., 22 to 23° C., 23 to 24°

C., 24 to 25° C., 25 to 26° C., 26 to 27° C., 27 to 28° C., 28 to 29° C., and 29 to 30° C. Extractive distillation conditions at block 304 may further include a reboiler range of 70 to 100° C. and all ranges and values there between including ranges of 70 to 73° C., 73 to 76° C., 76 to 79° C., 79 to 82° C., 82 to 85° C., 85 to 88° C., 88 to 91° C., 91 to 94° C., 94 to 97° C., and 97 to 100° C. Extractive distillation conditions at block 304 may further include an operation pressure in a range of 3 to 5 bar and all ranges and values there between including ranges of 3 to 3.2 bar, 3.2 to 3.4 bar, 3.4 to 3.6 bar, 3.6 to 3.8 bar, 3.8 to 4.0 bar, 4.0 to 4.2 bar, 4.2 to 4.4 bar, 4.4 to 4.6 bar, 4.6 to 4.8 bar, and 4.8 to 5.0 bar. Extractive distillation conditions at block 304 may further include a flowrate ratio of cooled effluent stream to soybean oil fed into extractive distillation unit 103 in a range of 10 to 15 and all ranges and values there between including ranges of 10 to 11, 11 to 12, 12 to 13, 13 to 14, and 14 to 15. An inlet for soybean oil may be disposed at the upper half of extractive distillation unit 103. An inlet for cooled effluent stream 13 may be disposed at the bottom of extractive distillation unit 103.

According to embodiments of the invention, first stream 31 includes 10 to 15 wt. % n-butane and 85 to 90 wt. % soybean oil. Second stream 32 may comprise 40 to 50 wt. % 1-butene, 40 to 50 wt. % unreacted n-butane, and 0.1 to 0.5 wt. % isobutene. Second stream 32 may further comprise less than 0.1 wt. % 2-butene.

According to embodiments of the invention, as shown in block 305, method 300 comprises separating second stream 32 to produce third stream 33 comprising primarily 1-butene. In embodiments of the invention, as shown in block 306, separating at block 305 includes distilling second stream 32 in first distillation unit 104 to produce fifth stream 35 comprising primarily n-butane and sixth stream 36 comprising primarily 1-butene and isobutene, collectively. In embodiments of the invention, fifth stream 35 further comprises less than 40 to 50 wt. % 2-butene. Sixth stream 36 comprises 99.5 to 99.9 wt. % 1-butene and 0.1 to 0.5 wt. % isobutene. Distilling at block 306 is performed at an overhead boiling range of 40 to 50° C. and all ranges and values there between including ranges of 40 to 41° C., 41 to 42° C., 42 to 43° C., 43 to 44° C., 44 to 45° C., 45 to 46° C., 46 to 47° C., 47 to 48° C., 48 to 49° C., and 49 to 50° C. Distilling at block 306 is performed at a reboiler range of 70 to 90° C. and all ranges and values there between including ranges of 70 to 72° C., 72 to 74° C., 74 to 76° C., 76 to 78° C., 78 to 80° C., 80 to 82° C., 82 to 84° C., 84 to 86° C., 86 to 88° C., 88 to 90° C. Distilling at block 306 is performed at an operating pressure in a range of 3 to 6 bar and all ranges and values there between including ranges of 3 to 3.2 bar, 3.2 to 3.4 bar, 3.4 to 3.6 bar, 3.6 to 3.8 bar, 3.8 to 4.0 bar, 4.0 to 4.2 bar, 4.2 to 4.4 bar, 4.4 to 4.6 bar, 4.6 to 4.8 bar, 4.8 to 5.0 bar, 5.0 to 5.2 bar, 5.2 to 5.4 bar, 5.4 to 5.6 bar, 5.6 to 5.8 bar, and 5.8 to 6.0 bar.

In embodiments of the invention, as shown in block 307, separating at block 305 comprises distilling sixth stream 36 in second distillation unit 105 to produce third stream 33 comprising primarily 1-butene and fourth stream 34 comprising primarily isobutene. According to embodiments of the invention, third stream 33 comprises 99.8 to 99.9 wt. % 1-butene and all ranges and values there between. Fourth stream 34 may comprise 99.1 to 99.8 wt. % isobutene and all ranges and values there between including 99.2 wt. %, 99.3 wt. %, 99.4 wt. %, 99.5 wt. %, 99.6 wt. %, and 99.7 wt. %. Distilling at block 307 is performed at an overhead boiling range of 40 to 50° C. and all ranges and values there between including ranges of 40 to 41° C., 41 to 42° C., 42 to 43° C., 43 to 44° C., 44 to 45° C., 45 to 46° C., 46 to 47° C., 47 to 48° C., 48 to 49° C., and 49 to 50° C. Distilling at block 307 is performed at a reboiler range of 70 to 90° C. and all ranges and values there between including ranges 70 to 72° C., 72 to 74° C., 74 to 76° C., 76 to 78° C., 78 to 80° C., 80 to 82° C., 82 to 84° C., 84 to 86° C., 86 to 88° C., 88 to 90° C. Distilling at block 307 is performed at an operating pressure in a range of 3 to 6 bar and all ranges and values there between including ranges of 3 to 3.2 bar, 3.2 to 3.4 bar, 3.4 to 3.6 bar, 3.6 to 3.8 bar, 3.8 to 4.0 bar, 4.0 to 4.2 bar, 4.2 to 4.4 bar, 4.4 to 4.6 bar, 4.6 to 4.8 bar, 4.8 to 5.0 bar, 5.0 to 5.2 bar, 5.2 to 5.4 bar, 5.4 to 5.6 bar, 5.6 to 5.8 bar, and 5.8 to 6.0 bar.

According to embodiments of the invention, method 300 comprises degassing first stream 31 in degasser 106 to produce liquid stream 21 comprising soybean oil and gaseous stream 20 comprising n-butane, as shown in block 308. In embodiments of the invention, at block 308, degasser 106 is operated at a temperature of 60 to 80° C. and all ranges and values there between including ranges of 60 to 62° C., 62 to 64° C., 64 to 66° C., 66 to 68° C., 68 to 70° C., 70 to 72° C., 72 to 74° C., 74 to 76° C., 76 to 78° C., and 78 to 80° C. Degasser 106 at block 308 may be operated at a pressure of 0.5 to 2 bar and all ranges and values there between including ranges of 0.5 to 0.6 bar, 0.6 to 0.7 bar, 0.7 to 0.8 bar, 0.8 to 0.9 bar, 0.9 to 1.0 bar, 1.0 to 1.1 bar, 1.1 to 1.2 bar, 1.2 to 1.3 bar, 1.3 to 1.4 bar, 1.4 to 1.5 bar, 1.5 to 1.6 bar, 1.6 to 1.7 bar, 1.7 to 1.8 bar, 1.8 to 1.9 bar, and 1.9 to 2.0 bar. In embodiments of the invention, method 300 further includes recycling liquid stream 21 comprising soybean oil to extractive distillation unit 103 as the solvent for extracting n-butane, as shown in block 309. Method 300 may further include recycling gaseous stream 20 comprising n-butane to the dehydrogenation zone of reaction unit 101, as shown in block 310.

Although embodiments of the present invention have been described with reference to blocks of FIGS. 2 and 3, it should be appreciated that operation of the present invention is not limited to the particular blocks and/or the particular order of the blocks illustrated in FIGS. 2 and 3. Accordingly, embodiments of the invention may provide functionality as described herein using various blocks in a sequence different than that of FIGS. 2 and 3.

In the context of the present invention, at least the following 20 embodiments are described. Embodiment 1 is a method. The method includes providing a mixture containing the olefin and a paraffin. The method further includes contacting the mixture with soybean oil under conditions such that the paraffin dissolves in the soybean oil at a higher rate than the olefin to form (1) a first stream containing the soybean oil and at least some of the paraffin of the mixture and (2) a second stream containing primarily the olefin.

Embodiment 2 is a method of producing a first olefin. The method includes dehydrogenating a paraffin to produce a mixture containing the first olefin and unreacted paraffin. The method further includes contacting the mixture with soybean oil under conditions such that the unreacted paraffin dissolves in the soybean oil at a higher rate than the first olefin to form (1) a first stream containing the soybean oil and at least some of the unreacted paraffin of the mixture and (2) a second stream containing primarily the first olefin. Embodiment 3 is the method of embodiment 2, wherein the dehydrogenating step produces the first olefin and a second olefin as isomers, and the method further includes, prior to the contacting step, isomerizing the second olefin to produce an additional amount of the first olefin in the mixture. Embodiment 4 is the method of any of embodiments 1 to 3, wherein the contacting step is performed in an extractive distillation column. Embodiment 5 is the method of any of embodiments 1 to 4, wherein the first stream contains at least 50 wt. % of the paraffin of the mixture. Embodiment 6 is the method of any of embodiments 1 to 5, wherein the conditions include an operating temperature in a range of 10 to 50° C.

Embodiment 7 is a method of producing 1-butene. The method includes dehydrogenating, in a dehydrogenation zone, n-butane to produce a first mixture containing 1-butene, 2-butene, isobutene, and unreacted n-butane. The method also includes processing, in an isomerization zone, the first mixture under isomerization conditions sufficient to isomerize 2-butene to form 1-butene. The method further includes contacting an effluent of the isomerization zone with soybean oil in an extractive distillation unit under extractive distillation conditions such that the unreacted n-butane dissolves in the soybean oil at a higher rate than the 1-butene and the isobutene to form (1) a first stream containing the soybean oil and at least some of the unreacted n-butane and (2) a second stream containing primarily 1-butene and isobutene. In addition, the method includes separating the second stream to produce a third stream containing primarily 1-butene. Embodiment 8 is the method of embodiment 7, wherein the first stream contains at least 50 wt. % of the unreacted n-butane. Embodiment 9 is the method of either of embodiments 7 or 8, wherein the effluent of the isomerization zone contains less than 0.1 wt. % 2-butene. Embodiment 10 is the method of any of embodiments 7 to 9, wherein the extractive distillation conditions include an operating temperature of 10 to 50° C. and an operating pressure of 3 to 5 bar. Embodiment 11 is the method of any of embodiments 7 to 10, wherein the second stream further contains n-butane and 2-butene and the separating further produces a fourth stream containing primarily isobutene, and a fifth stream containing primarily n-butane. Embodiment 12 is the method of embodiment 11, wherein the fifth stream further contains less than 40 to 50 wt. % 2-butene. Embodiment 13 is the method of either of embodiments 11 or 12, wherein the separating includes distilling the second stream in a first distillation column to produce the fifth stream containing n-butane and less than 40 to 50 wt. % 2-butene and a sixth stream containing primarily 1-butene and isobutene, collectively. The method further includes distilling the sixth stream to produce the third stream containing primarily 1-butene and fourth stream containing primarily isobutene. Embodiment 14 is the method of any of embodiments 7 to 13, wherein the third stream contains 99 to 99.9 wt. % 1-butene. Embodiment 15 is the method of any of embodiments 7 to 14, further including cooling the effluent of the isomerization zone before the contacting step. Embodiment 16 is the method of any of embodiments 7 to 15, further including degassing the first stream to produce a recycle soybean oil stream and a recycle n-butane stream. The method further includes recycling the recycle soy bean oil stream to the extractive distillation unit for extracting n-butane, and recycling the recycle n-butane stream to the dehydrogenation zone. Embodiment 17 is the method of any of embodiments 7 to 16, wherein the dehydrogenating is performed in the presence of a catalyst containing platinum, tin, alumina or combinations thereof. Embodiment 18 is the method of any of embodiments 7 to 17, wherein the dehydrogenating is performed at a dehydrogenation temperature of 400 to 550° C. and a dehydrogenation pressure of 0 to 15 bar. Embodiment 19 is the method of any of embodiments 7 to 18, wherein the isomerizing is performed in the presence of a catalyst containing alpha ($\alpha$)-alumina, theta ($\theta$)-alumina, gamma ($\gamma$)-alumina, or combinations thereof. Embodiment 20 is the method of any of embodiments 7 to 19, wherein the isomerizing is performed at an isomerization temperature of 400 to 550° C. and an isomerization pressure of 10 to 15 bar.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method comprising:
   providing a mixture comprising an olefin and a paraffin; and
   contacting the mixture with soybean oil under conditions such that the paraffin dissolves in the soybean oil at a higher rate than the olefin to form (1) a first stream comprising the soybean oil and at least some of the paraffin of the mixture and (2) a second stream comprising primarily the olefin.

2. A method of producing a first olefin, the method comprising:
   dehydrogenating a paraffin to produce a mixture comprising the first olefin and unreacted paraffin; and
   contacting the mixture with soybean oil under conditions such that the unreacted paraffin dissolves in the soybean oil at a higher rate than the first olefin to form (1) a first stream comprising the soybean oil and at least some of the unreacted paraffin of the mixture and (2) a second stream comprising primarily the first olefin.

3. The method of claim 2, wherein the dehydrogenating step produces the first olefin and a second olefin as isomers, and the method further comprises, prior to the contacting step, isomerizing the second olefin to produce an additional amount of the first olefin in the mixture.

4. The method of claim 1, wherein the contacting step is performed in an extractive distillation column.

5. The method of claim 1, wherein the first stream comprises at least 50 wt. % of the paraffin of the mixture.

6. The method of claim 1, wherein the conditions comprise an operating temperature in a range of 10 to 50° C.

7. A method of producing 1-butene, the method comprising:
   dehydrogenating, in a dehydrogenation zone, n-butane to produce a first mixture comprising 1-butene, 2-butene, isobutene, and unreacted n-butane;
   processing, in an isomerization zone, the first mixture under isomerization conditions sufficient to isomerize 2-butene to form 1-butene;
   contacting an effluent of the isomerization zone with soybean oil in an extractive distillation unit under extractive distillation conditions such that the unreacted n-butane dissolves in the soybean oil at a higher rate than the 1-butene and the isobutene to form (1) a first stream comprising the soybean oil and at least some of the unreacted n-butane and (2) a second stream comprising primarily 1-butene and isobutene; and separating the second stream to produce a third stream comprising primarily 1-butene.

8. The method of claim 7, wherein the first stream comprises at least 50 wt. % of the unreacted n-butane.

9. The method of claim 7, wherein the effluent of the isomerization zone comprises less than 0.1 wt. % 2-butene.

10. The method of claim 7, wherein the extractive distillation conditions include an operating temperature of 10 to 50° C. and an operating pressure of 3 to 5 bar.

11. The method of claim 7, wherein the second stream further comprises n-butane and 2-butene and the separating further produces a fourth stream comprising primarily isobutene, and a fifth stream comprising primarily n-butane.

12. The method of claim 11, wherein the fifth stream further comprises less than 40 to 50 wt. % 2-butene.

13. The method of claim 12, wherein the separating comprises:
distilling the second stream in a first distillation column to produce the fifth stream comprising n-butane and less than 40 to 50 wt. % 2-butene and a sixth stream comprising primarily 1-butene and isobutene, collectively;
distilling the sixth stream to produce the third stream comprising primarily 1-butene and fourth stream comprising primarily isobutene.

14. The method of claim 7, wherein the third stream comprises 99 to 99.9 wt. % 1-butene.

15. The method of claim 7, further comprising cooling the effluent of the isomerization zone before the contacting step.

16. The method of claim 7, further comprising:
degassing the first stream to produce a recycle soybean oil stream and a recycle n-butane stream; and
recycling the recycle soy bean oil stream to the extractive distillation unit for extracting n-butane;
recycling the recycle n-butane stream to the dehydrogenation zone.

* * * * *